United States Patent
Buist, Sr.

(10) Patent No.: US 10,772,705 B2
(45) Date of Patent: Sep. 15, 2020

(54) HAND OPERATED DENTAL INSTRUMENT

(71) Applicant: Charles Buist, DMD, PA, Hilton Head Island, SC (US)

(72) Inventor: Charles Buist, Sr., Irmo, SC (US)

(73) Assignee: Charles Buist, DMD, PA, Hilton Head Island, SC (US)

( * ) Notice: Subject to any disclaimer, the term of this patent is extended or adjusted under 35 U.S.C. 154(b) by 246 days.

(21) Appl. No.: 16/108,539

(22) Filed: Aug. 22, 2018

(65) Prior Publication Data
US 2020/0060788 A1 Feb. 27, 2020

(51) Int. Cl.
*A61C 1/14* (2006.01)
*A61C 3/02* (2006.01)
*A61B 17/16* (2006.01)

(52) U.S. Cl.
CPC ............. *A61C 1/147* (2013.01); *A61C 1/141* (2013.01); *A61C 1/144* (2013.01); *A61C 3/02* (2013.01); *A61B 17/1617* (2013.01)

(58) Field of Classification Search
CPC .......... A61C 1/14; A61C 1/141; A61C 1/142; A61C 1/144; A61C 1/147; B23B 31/1175; Y10T 279/17829; Y10T 279/17965; Y10T 279/17794
USPC ........................................................ 433/147
See application file for complete search history.

(56) References Cited

U.S. PATENT DOCUMENTS

| 233,486 | A | * | 10/1880 | Donaldson | |
|---|---|---|---|---|---|
| 5,481,949 | A | * | 1/1996 | Yen | B25B 23/0035 279/24 |
| 6,698,320 | B2 | * | 3/2004 | Hu | B25B 23/0035 81/438 |
| 9,498,273 | B2 | * | 11/2016 | Thoren | A61B 17/8891 |
| 2011/0236853 | A1 | | 9/2011 | Shimoo | |
| 2011/0243673 | A1 | | 10/2011 | Svagr | |

FOREIGN PATENT DOCUMENTS

| CN | 2478552 | 2/2002 |
|---|---|---|
| CN | 106725718 | 5/2017 |
| DE | 102013225947 | 6/2015 |
| EP | 2110097 | 10/2009 |
| KR | 101628648 | 6/2016 |
| WO | WO2016024681 | 2/2016 |

\* cited by examiner

*Primary Examiner* — Ralph A Lewis
(74) *Attorney, Agent, or Firm* — Burr & Forman LLP; Hunter S. Freeman (57) ABSTRACT

The present invention relates to a hand operated dental instrument that allows a user to manually operate tool bits that are ordinarily operated by a power operated tool. Then invention includes a handle that carries a shaft; a bore-hole extending through at least a portion of the shaft for receiving a tool bit; an elevated stop disposed in the bore-hole for engaging at least a portion of a tool bit that is inserted into the bore-hole; a securing ring receiving slot disposed in the shaft and is in fluid communication with the bore-hole; and a securing ring that when placed in the securing ring receiving slot presses at least a portion of the tool bit towards the elevated stop so that when the shaft is rotated, the tool bit rotates.

20 Claims, 6 Drawing Sheets

HAND OPERATED DENTAL INSTRUMENT

BACKGROUND OF THE INVENTION

1) Field of the Invention

The present invention relates to a hand operated dental instrument. More specifically, the present invention relates to an instrument that is adapted to receive various tool bits, such as drill bits, and to manually torque or rotate the tool bit by torqueing or rotating the present invention.

2) Description of Related Art

Electric drills are well known in the field of dentistry. However, often times, the material to be removed or to otherwise be drilled is very small and/or requires precise placement of the drill. In such instances, the high angular velocity used by electric drill makes it very difficult to remove only small amounts and/or to operate the drill with the level of precision required by the dental procedure. It would be advantageous if the angular velocity of the drill bit could be better controlled and slowed.

Another drawback of an electric drill is that the user of the drill has very little feel for what material is being drilled or how much material is being removed. Therefore, it would also be advantageous if the user were provided more feel of what and how much material were being drilled.

Accordingly, it is an object of the present invention to provide a hand operated instrument that allows the drill bit to be rotated by hand and at the desired speed of the user.

Accordingly, it is an object of the present invention to provide a hand operated instrument that provides the user a greater level of control of what is being drilled and how much material is being removed by the drill.

SUMMARY OF THE INVENTION

The above objectives are accomplished according to the present invention by providing A hand operated dental instrument comprising: a handle; a shaft having an outer surface, a distal end and a proximal end wherein said proximal end is carried by said handle; a bore-hole defined in at least a portion of said shaft and extending from said distal end of said shaft towards said proximal end of said shaft, wherein said bore-hole is defined by at least one inner side wall and is adapted to receive at least a portion of a tool bit; an elevated stop defined in said bore-hole for engaging a portion of the tool bit that is inserted into said bore-hole, wherein said elevated stop comprises: a first stop wall that extends from said at least one inner side wall of said bore-hole in a direction that is towards the longitudinal axis of said bore-hole and is generally perpendicular to the longitudinal axis of said shaft; and, a second stop wall the extends from said first stop wall in a direction that is generally parallel to the longitudinal axis of said shaft; a securing ring receiving slot defined in said shaft, wherein at least a portion of said securing ring receiving slot extends through said at least one inner side wall of said bore-hole so that said securing ring receiving slot is in fluid communication with said bore-hole; a securing ring, at least a portion of which is received by said securing ring receiving slot so that at least a portion of said securing ring extends into said bore-hole so that said securing ring engages a surface of the tool bit that has been inserted into said bore-hole so that said securing ring presses at least a portion of the tool bit towards at least one of said first stop wall and said second stop wall of said elevated stop; and, whereby when at least a portion of the tool bit is inserted into said bore-hole and said securing ring is received by said securing ring receiving slot, said elevated stop engages at least a portion of the tool bit and said securing ring presses at least a portion of the tool bit towards said elevated stop to maintain engagement of the tool bit and said elevated stop so that rotation of said handle causes the tool bit to rotate.

In another embodiment, the hand operated dental instrument further comprises an access opening disposed in said shaft and is in fluid communication with said securing ring receiving slot for allowing the user to remove said securing ring from within said securing ring receiving slot. In at least one embodiment, said access opening is in fluid communication with said bore-hole and extends from a point that is generally adjacent to said securing ring receiving slot to said distal end of said shaft.

In another embodiment, said shaft is carried by said handle so that said shaft extends outwardly from said handle along the longitudinal axis of said handle and said first stop wall of said elevated stop extends from said at least one inner side wall to a midpoint of said bore-hole.

In another embodiment, said securing ring receiving slot extends into said bore-hole at a point that is generally above said second stop wall of said elevated stop so that said securing ring presses the tool bit towards said second stop wall of said elevated stop. In another embodiment, said securing ring receiving slot extends around the entire outer surface of said shaft.

In another embodiment, said bore-hole is defined by three or more inner side walls. In yet another emobodiment, said securing ring is adjustable so that the pressure that said securing ring applies to at least a portion of the tool bit may be adjusted.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Referring now to FIGS. 1-5, the present invention is shown generally as 1 and relates to a hand operated dental instrument capable of receiving and securing various tool bits (both rotary and non-rotary in nature), such as drill bits, flat head bits, Phillips head bits, cutting bits, planing or shaping bits (such as chisel bits) as well as any other tool bits that are generally known, whether such bits are rotary or non-rotary in nature. As can be seen in FIGS. 2-5, once secured to the dental instrument 1, the tool bit can be used by maneuvering the instrument 1 in the manner necessary to achieve the desired result with the tool bit.

The dental instrument 1 includes a handle 2 that may be gripped by the user and used to manipulate or move the dental instrument. Generally speaking, the handle 2 can be rotated, spun, reciprocated or moved in an manner desired to cause the tool bit to move in the desired manner. The dental instrument further includes a shaft 4 that has a proximal end 4b that is carried by the handle 2 and a distal end 4a that is adapted for receiving and securing the tool bits 16. The shaft's proximal end 4b may be integral with the handle 4 or may be removably attached thereto. In the present embodiment, the shaft is cylindrically shaped and, thus, has a radiused outer surface 5. In alternate embodiments, however, the shaft's outer surface 5 could have any number of cross-sectional shapes that are generally known such as square, rectangular, hexagonal, octagonal and/or triangular. In such cases, the shaft would have a number of sides that form the outer surface of the shaft. In the shown embodiment, shaft 4 is shown as having varying diameters. In alternate embodiments, shaft could have a single diameter (or width in embodiments where shaft is not cylindrically shaped), a constant diameter or could even be tapered.

In the shown embodiment, the shaft 4 is carried by the handle 2 so that the shaft extends along the longitudinal axis (A) of the handle 2 such that longitudinal axis (A) of the shaft 4 is the same as the longitudinal axis for the handle. As discussed more fully in FIGS. 6A-C and 7A-C, in alternate embodiments, however, the shaft 4 may be offset from the longitudinal axis (A) of the handle 2. In even further embodiments, the shaft 4 could extend at an angle from the handle 2 so that the shaft 4 is in an angled relation with the handle. This angled relationship could provide the user additional with additional torqueing force for rotating the shaft 4.

Figure 1:
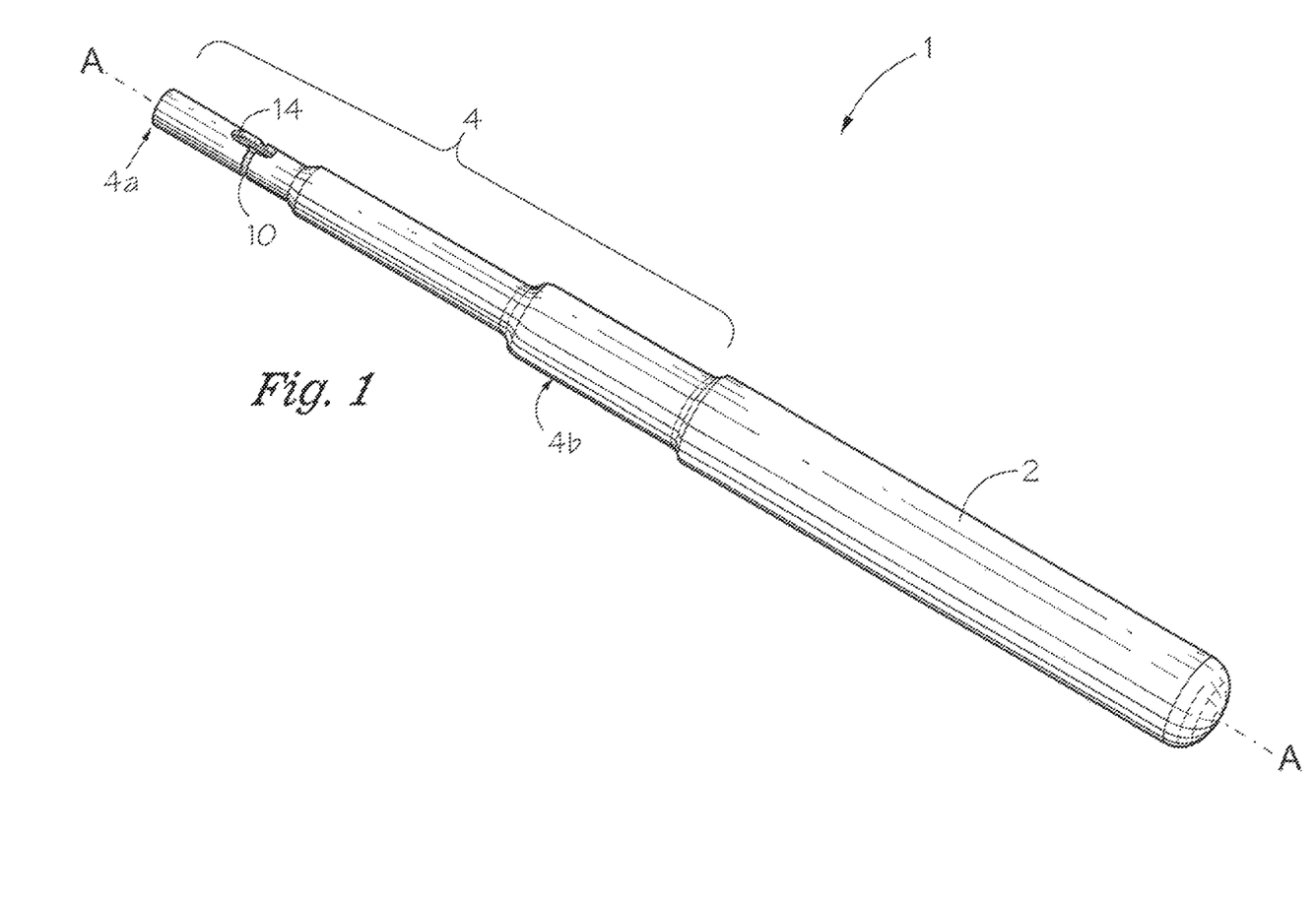
FIG. 1 shows a perspective view of an embodiment of the present invention.
Figure 2:
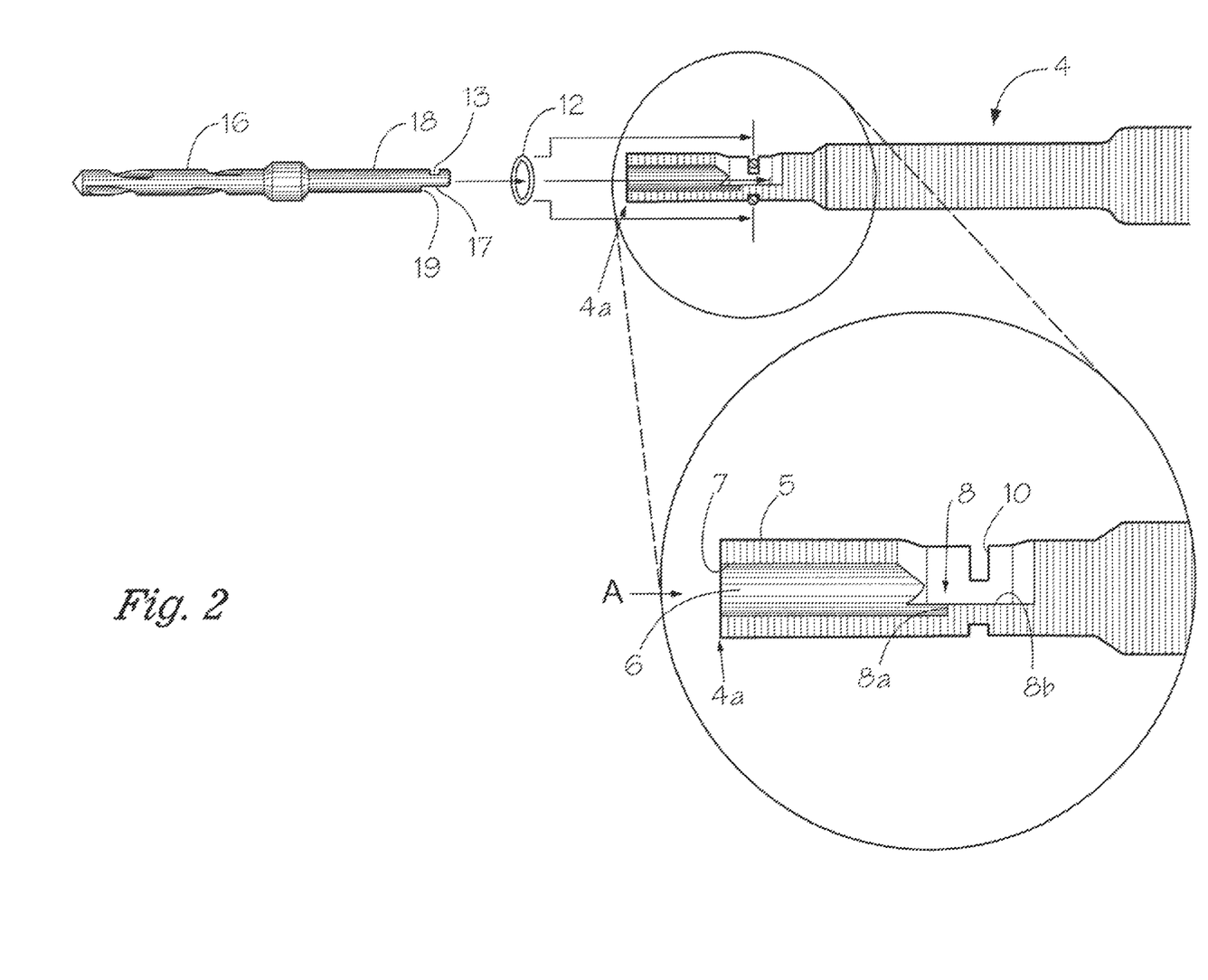
FIG. 2 shows a side elevation view with a cross-sectional view of a portion of an embodiment of the present invention.
Figure 3:
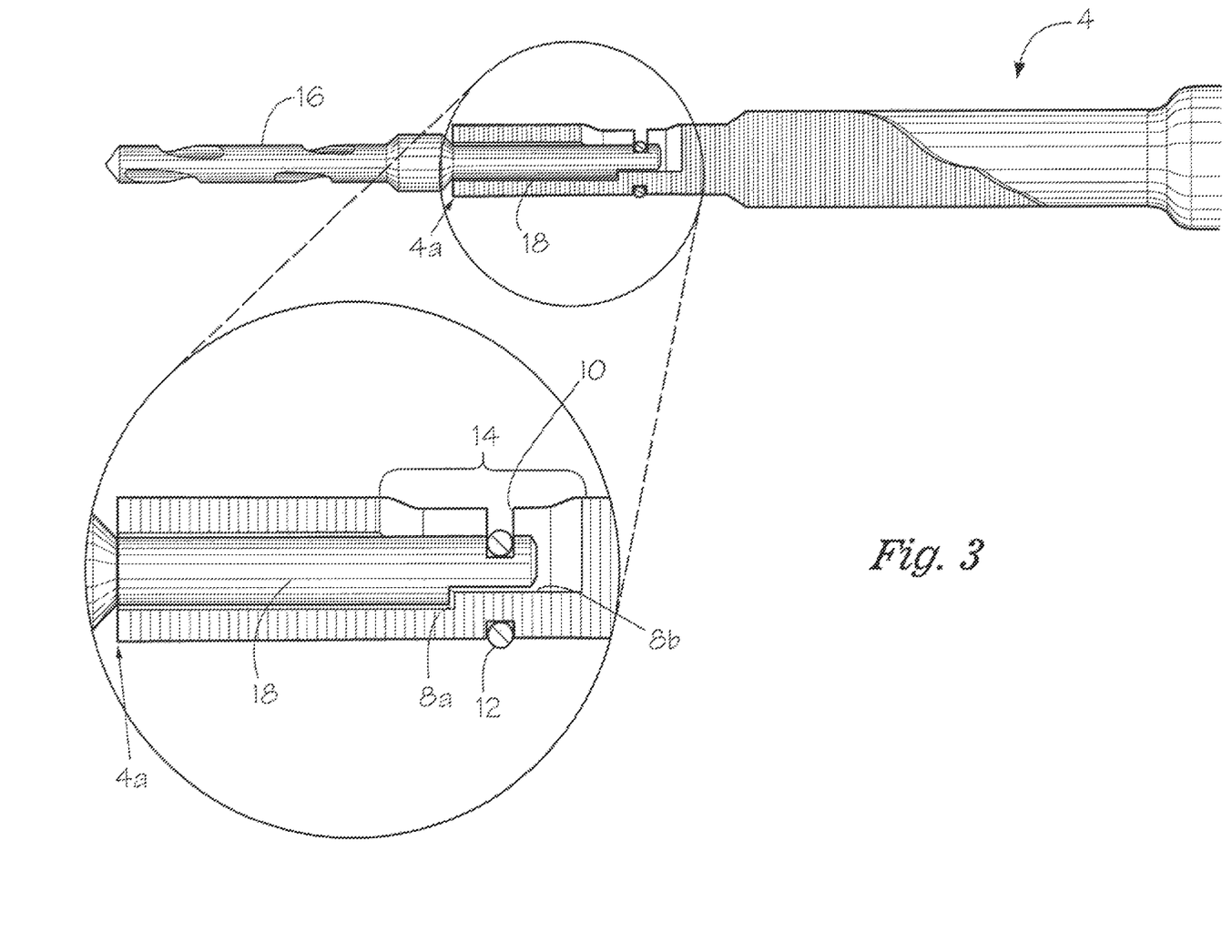
FIG. 3 shows another a side elevation view with a cross-sectional view of a portion of an embodiment of the present invention.

As seen in FIGS. 2-3, a bore-hole 6 is formed in at least a portion of the shaft 4 and extends from the distal end 4a of the shaft to a point that is closer to the proximal end 4b of the shaft. This bore-hole 6 creates a channel into which tool bits 16 can be inserted. In one embodiment, the channel created by the bore-hole 6 is completely enclosed creating a tunnel through a portion of the shaft 4. In alternate embodiments, however, the bore-hole 6 could define a channel that is not completely enclosed but is instead generally "U" or horseshoe shaped. In one embodiment, the bore-hole 6 extends generally along the longitudinal axis (A) of the shaft so that the handle's longitudinal axis (A) extends generally through the center of the bore hole 6. In alternate embodiments, the bore-hole 6 could be offset from the shaft's longitudinal axis (A) so that the handle's longitudinal axis (A) does not extend through the center of the bore hole. In the shown embodiment the bore-hole 6 has a cross sectional shape that is circular. In such an embodiment, the bore-hole is defined by a single curved inner side wall 7. In alternate embodiments, the bore-hole 6 could be defined by a plurality of inner side walls giving the bore-hole a cross sectional shape that could be any number of shapes generally known such as "U" or horseshoe shaped, square, rectangular, hexagonal, octagonal and/or triangular. In embodiments where the bore-hole is not fully enclosed, the at least one inner side wall 7 would not connect to itself, or in the case of multiple inner side walls, at least two of the inner side walls would not connect to one another.

The dental instrument further includes an elevated stop 8 disposed in the bore-hole 6 that is adapted to engage at least a portion of the tool bit shaft 18 once it has been inserted into the bore-hole 6. Generally speaking, the elevated stop 8 engages and secures the tool bit's shaft 18 to ensure that the manipulation of the handle 2 or shaft 4 will cause the desired movement and/or use of the tool bit 16. The elevated stop 8 comprises a first stop wall 8a that extends inwardly from the inner side wall 7 forming bore-hole 6 and generally towards the center of the bore-hole. In the embodiments where the bore-hole 6 is formed by multiple inner side walls, the first stop wall 8a could extend inwardly from two or more of the inner side walls 7. In the shown embodiment, the first stop wall 8a of the elevated stop 8, extends in a direction that is generally perpendicular to the longitudinal axis (A) of the shaft 4. In alternate embodiments, however, the first stop wall 8a could extend in an angular relation to the shaft's longitudinal axis (A), where that angle is either greater than or less than 90 degrees. In the shown embodiment, the first stop wall 8a engages the tool bit shaft 18 (a portion of which typically will have a corresponding stop wall 19) to ensure that the tool bit shaft 18 may only be inserted to a desired depth within the bore-hole, thus, ensuring that at least a portion of the tool bit 16 protrudes from the bore-hole 6.

The elevated stop 8 further includes a second stop wall 8b that extends from the first stop wall 8a in a direction that is preferably generally parallel to the shaft's longitudinal axis (A). The second stop wall 8b has a generally flat surface that engages the drill bit's shaft 18 (a portion of which typically will have a corresponding flat surface 17) so that when the handle 2 or shaft 4 of the present invention is rotated, the drill bit 16 will also rotate. In alternate embodiments, the second stop wall 8b could extend in an angled relation to the shaft's longitudinal axis (A) (said longitudinal axis of the shaft being shown as (B) on FIGS. 6A-C and 7A-C).

The present invention further includes a securing ring receiving slot 10 that is defined in the outer surface 5 of the shaft 4 and is adapted to receive a securing ring 12. This securing ring receiving slot 10 is disposed in the shaft 4 such that at least a portion of the slot 10 extends through one or more of the inner side walls 7 that define the bore-hole 6. Thus, at least a portion of the securing ring receiving slot 10 is placed in fluid communication with the bore-hole 6. The securing ring receiving slot 10 may extend around the shaft's entire outer surface 5 so that the slot 10 extends around the entire circumference or perimeter of the of the shaft 4. Alternatively, the securing ring receiving slot 10 only extends around a portion of the shaft's outer surface 5. In at least one embodiment, the securing ring receiving slot 10 extends through one or more of the inner side walls 7 at a point that is directly above or opposite from the second stop wall 8b and the flat surface created thereby.

Figures 4, 5:
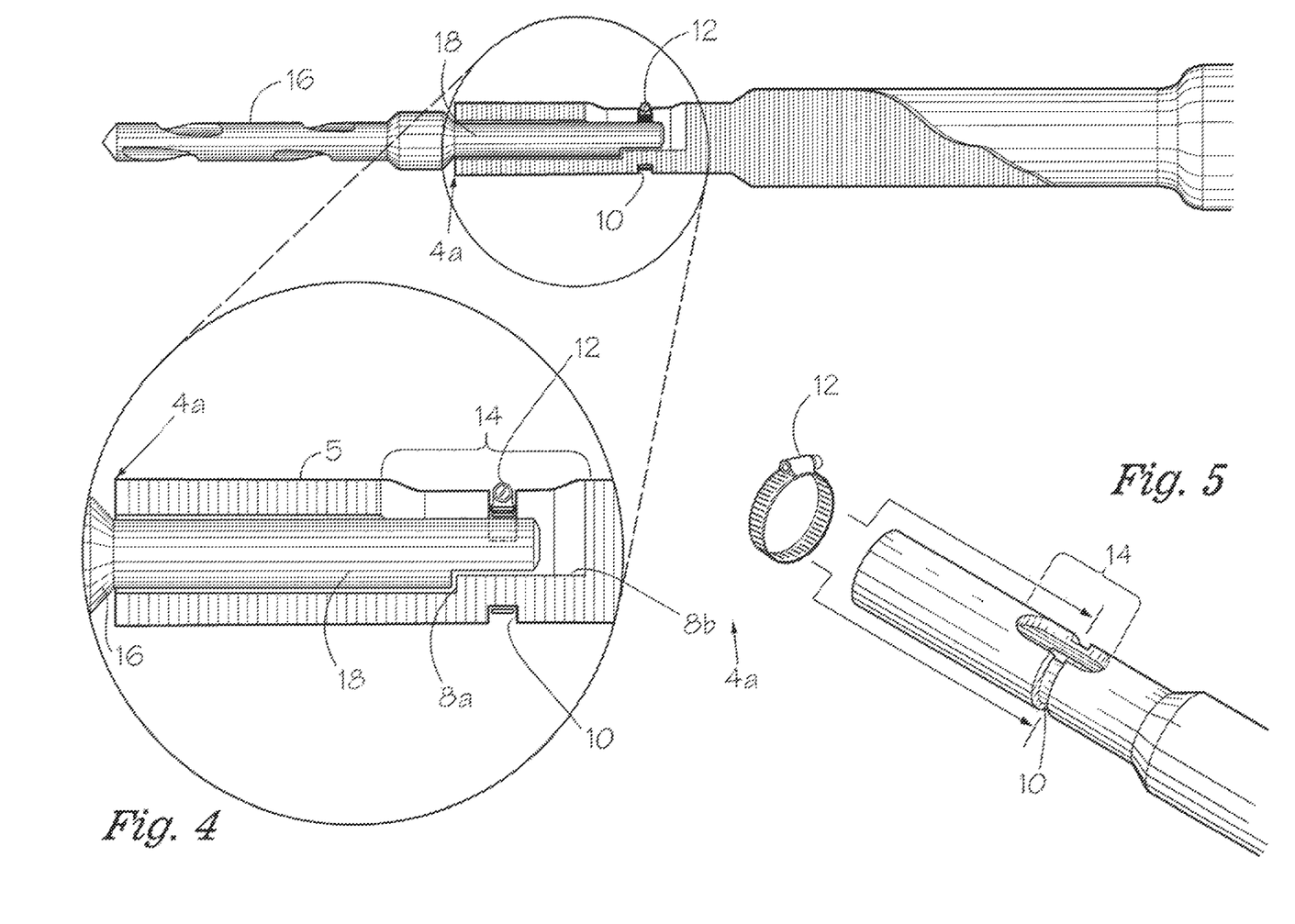
FIG. 4 shows another side elevation view with a cross-sectional view of a portion of another embodiment of the present invention.
FIG. 5 shows a perspective view of a portion of another embodiment of the present invention.

When placed in the securing ring receiving slot 10, the securing ring 12 extends into at least a portion of the bore-hole and engages at least a portion of the tool bit's shaft 18 (which typically will have a slot 13 disposed in the tool bit's shaft 18 that corresponds to the securing ring receiving slot 10). The securing ring 12 may be made of an elastic material or can otherwise be adjustable so that the diameter of the securing ring can be adjusted to be greater or smaller. As shown in FIGS. 2-3, the securing ring 12 could comprise an O-ring made of any elastic material known in the art. Alternatively, and as shown in FIGS. 4-5, the securing ring 12 could comprise a pipe ring or any other mechanism, such as a clamp, that allows the diameter of the securing ring to be adjusted. The securing ring 12 presses the tool bit's shaft 18 towards the elevated stop 8 to ensure that rotation of the handle 2 or shaft 4 of the present invention will cause the tool bit 16 to rotate. Preferably, the securing ring 12 maintains contact between at least a portion of the drill bit shaft 18 and the second stop wall 8b. However, the securing ring 12 is meant to press the tool bit's shaft 18 towards at least one of the first and second stop walls 8a and 8b. Regardless of whether contact is made with both stop walls, the force applied by the securing ring 12 is sufficient to allow the elevated stop 8 to engage a portion of the tool bit shaft 18 to ensure rotation of the tool bit 16 when the handle 2 or shaft 4 of the present invention is rotated.

The present invention further includes an access opening 14 that is defined in the shaft 4 so that the access opening 14 extends through the inner side wall 7 of the bore-hole, thus placing the access opening 14 in fluid communication with the bore-hole. This access opening 14 allows the user to access the securing ring 12 so as to remove the securing ring from the securing ring receiving slot 10. In one embodiment the access opening 14 extends through securing ring slot 10 as shown in FIGS. 1-5. In alternate embodiments, however, the access opening 14 could be disposed adjacent to the securing ring receiving slot 10. In some embodiments, access opening 14 is in fluid communication with securing ring receiving slot 10 but not with bore-hole 6.

Figure 6A:
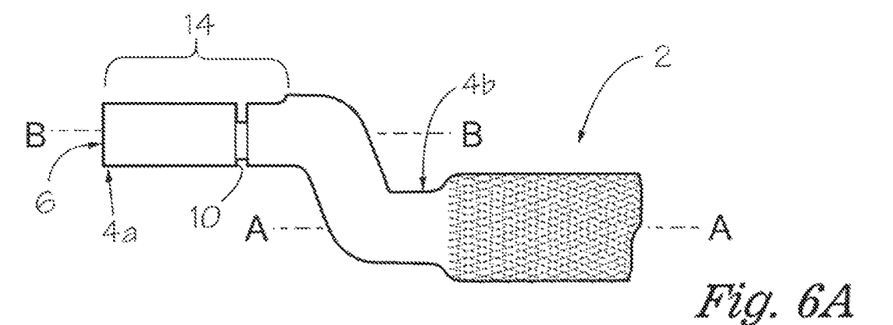
FIG. 6A shows a side elevation view of a portion of another embodiment of the present invention.
Figure 6B:
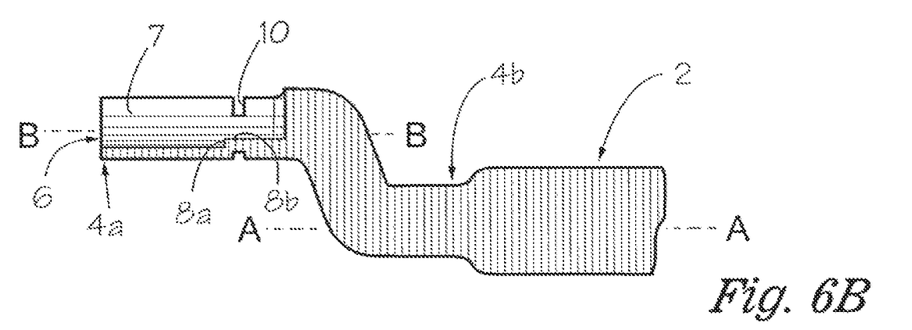
FIG. 6B shows a cross-sectional view of a portion of another embodiment of the present invention.
Figure 6C:
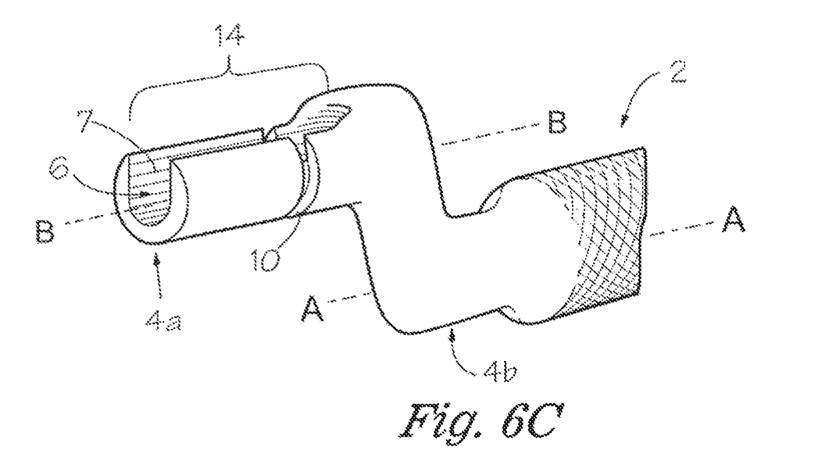
FIG. 6C shows a perspective view of a portion of another embodiment of the present invention.

Referring now to FIGS. 6A-6C, another embodiment of the invention is shown. In this embodiment, the shaft 4 is offset from the handle such that the shaft's longitudinal axis (B) is parallel to but spaced from the longitudinal axis (A) of the handle 2. By offsetting the shaft from the handle, the user is able to more easily use the tool to reach the molars and other teeth located in the rear of the patient's jaw. As can be seen in these figures, the shaft may be offset from the handle by means of using a curved or bent portion of the shaft. In other embodiments (not shown) the tool could include a connector piece that would vertically space the shaft from the handle in the desired manner.

As can also be seen in these figures, the access opening 14 may extend from the shaft's distal end 4a to a desired point closer to the proximal end 4b of the shaft and/or adjacent to the securing ring receiving slot 10. In this embodiment, the bore-hole 6 would not be fully enclosed such that the inner side wall 7 forming the bore-hole 6 would not connect, creating a substantially "U" shaped horse-shoe shaped bore-hole 6.

In embodiments where the bore-hole is not fully enclosed, the access opening 14 would extend to the tip of the distal end 4a of the shaft 4 and along the entire the length of the bore-hole 6 or a substantial portion thereof. In embodiments, such as the one shown in FIGS. 7A-C, where the bore-hole 6 is defined by multiple inner side walls 7a-7d, the access opening 14 would extend from the distal end 4a in a manner where at least a portion of two of the inner side walls would not connect to one another.

Figure 7A:
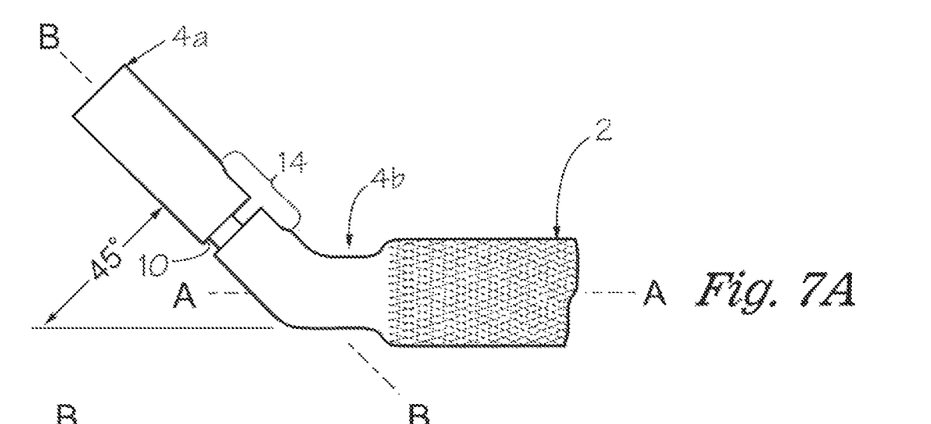
FIG. 7A shows a side elevation view of a portion of another embodiment of the present invention.
Figure 7B:
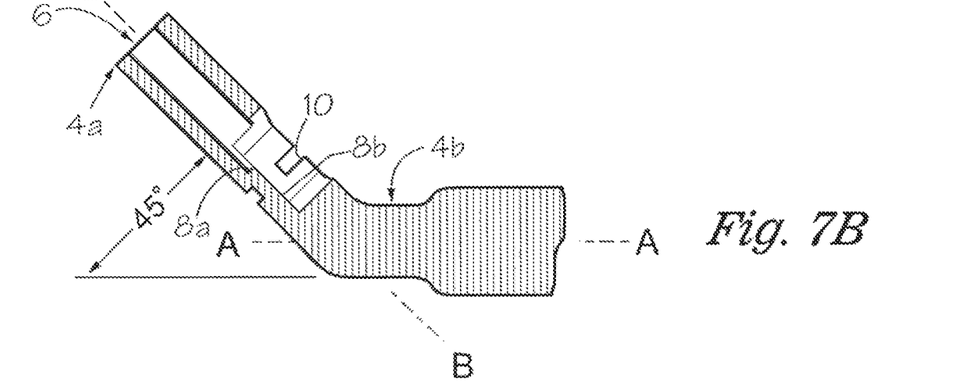
FIG. 7B shows a cross-sectional view of a portion of another embodiment of the present invention; and, FIG. 7C shows a perspective view of a portion of another embodiment of the present invention.
Figure 7C:
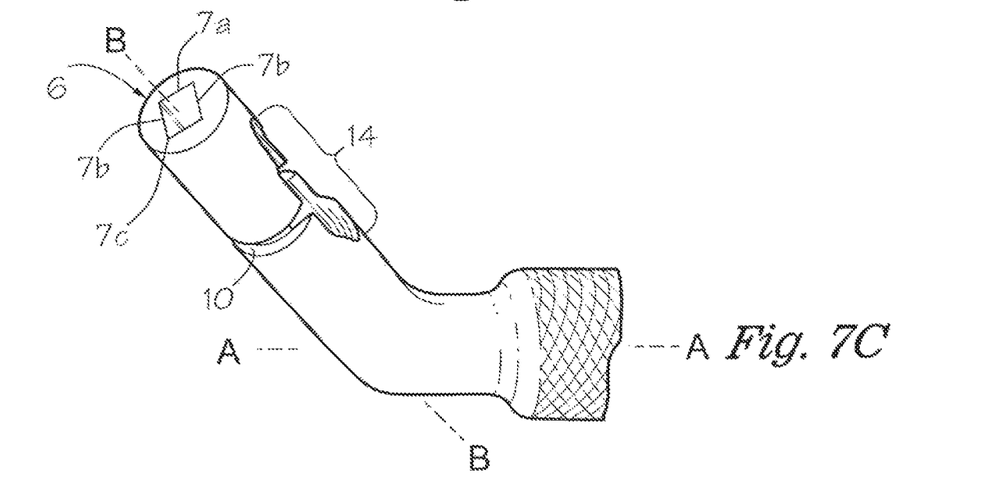

Referring now to FIGS. 7A-C, another embodiment of the invention may be seen. In this embodiment, the shaft 4 extends from the handle 2 in an angled manner so that the shaft's longitudinal axis (B) intersects the handle's longitudinal axis (A) at an angle. In at least one embodiment, the angle between the shaft 4 and the handle 2 is approximately 45 degrees. In alternate embodiments, the angle between the shaft and the handle could be greater than or equal to 0 degrees but less than or equal to 90 degrees or greater than or equal to 90 degrees but less than or equal to 180 degrees.

As can be seen in these figures, the bore-hole 6 can be defined by a plurality of inner side walls 7a-7d. In such embodiments, the need for the elevated stop 8 would be alleviated as the two or more of the inner side walls 7a-7d would engage a tool bit shaft 17 having an equal number of corresponding sides (not shown) so that when the shaft 4 or handle 4 is rotated, the tool bit 16 rotates.

In operation, a tool bit 16 is inserted into the bore-hole 6 so that at least a portion of the tool bit's shaft 18 is engaged by the elevated stop 8. Ordinarily, the first stop wall 8a will contact and engage a corresponding stop wall 19 formed in shaft of the tool bit and the second stop wall 8b will contact and engage a corresponding flat surface 19 formed in the shaft of the tool bit. Once the tool bit 16 has been inserted into the bore-hole 6, the securing ring 12 can be placed in the securing ring slot 10. Once in place, the securing ring presses at least a portion of the tool bit shaft 18 towards the elevated stop. In cases where the tool bit includes a slot 13, the securing ring 12 will engage the slot 13 of the tool bit. In a preferred embodiment, the securing ring 12 will cause the second stop wall 8b to contact or otherwise engage the flat surface 19 formed in the tool bit's shaft 18 so that when the handle 2 or the shaft 4 of the present invention is rotated, spun or subjected to a torqueing force, the tool bit 16 is caused to rotate. The securing ring 12 also preferably provides enough pressure on at least a portion of the tool bit shaft 18 that it reduces or prevents the tool bit shaft 18 from sliding out of the bore-hole 6. This preferred objective is more easily accomplished when the tool bit shaft 18 includes a slot 13. Thus, manipulation of the handle 2 or shaft 4 of the present invention will allow the tool bit to be operated in a desired manner. Because the tool is hand operated, the user will have better control over the speed of and pressure under which the tool bit is operated. Further, the hand operated nature of the present invention will also minimize the effect of accidental placement of the tool bit so that misplacement of the tool bit 16 will result in less damage to the area being subjected to the tool bit.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A hand operated dental instrument comprising:
   a handle;
   a shaft having an outer surface, a distal end and a proximal end wherein said proximal end is carried by said handle;
   a bore-hole defined in at least a portion of said shaft and extending from said distal end of said shaft towards said proximal end of said shaft, wherein said bore-hole is defined by at least one inner side wall and is adapted to receive at least a portion of a tool bit;
   an elevated stop defined in said bore-hole for engaging a portion of the tool bit that is inserted into said bore-hole, wherein said elevated stop comprises:
      a first stop wall that extends from said at least one inner side wall of said bore-hole in a direction that is towards the longitudinal axis of said bore-hole and is generally perpendicular to the longitudinal axis of said shaft; and,
      a second stop wall the extends from said first stop wall in a direction that is generally parallel to the longitudinal axis of said shaft;
   a securing ring receiving slot defined in said shaft, wherein at least a portion of said securing ring receiving slot extends through said at least one inner side wall of said bore-hole so that said securing ring receiving slot is in fluid communication with said bore-hole;
   a securing ring, at least a portion of which is received by said securing ring receiving slot so that at least a portion of said securing ring extends into said bore-hole so that said securing ring engages a surface of the tool bit that has been inserted into said bore-hole so that said securing ring presses at least a portion of the tool bit towards at least one of said first stop wall and said second stop wall of said elevated stop; and,
   whereby when at least a portion of the tool bit is inserted into said bore-hole and said securing ring is received by said securing ring receiving slot, said elevated stop engages at least a portion of the tool bit and said securing ring presses at least a portion of the tool bit towards said elevated stop to maintain engagement of the tool bit and said elevated stop so that rotation of said handle causes the tool bit to rotate.

2. The hand operated dental instrument of claim 1 further comprising an access opening disposed in said shaft and is in fluid communication with said securing ring receiving slot for allowing the user to remove said securing ring from within said securing ring receiving slot.

3. The hand operated dental instrument of claim 2, wherein said access opening is in fluid communication with said bore-hole and extends from a point that is generally adjacent to said securing ring receiving slot to said distal end of said shaft.

4. The hand operated dental instrument of claim 1 wherein said shaft is carried by said handle so that said shaft extends outwardly from said handle along the longitudinal axis of said handle.

5. The hand operated dental instrument of claim 1 wherein said first stop wall of said elevated stop extends from said at least one inner side wall to a midpoint of said bore-hole.

6. The hand operated dental instrument of claim 1 wherein said securing ring receiving slot extends into said bore-hole at a point that is generally above said second stop wall of said elevated stop so that said securing ring presses the tool bit towards said second stop wall of said elevated stop.

7. The hand operated dental instrument of claim 1 wherein said securing ring receiving slot extends around the entire outer surface of said shaft.

8. The hand operated dental instrument of claim 1 wherein said bore-hole is defined by three or more inner side walls.

9. The hand operated dental instrument of claim 1 wherein said securing ring is adjustable so that the pressure that said securing ring applies to at least a portion of the tool bit may be adjusted.

10. A hand operated dental instrument comprising:
    a handle;
    a shaft having an outer surface, a distal end and a proximal end wherein said proximal end is carried by said handle;
    a generally cylindrical bore-hole defined in a distal end of said shaft and extending longitudinally through at least a portion of said shaft, wherein said bore-hole is adapted to receive at least a portion of a tool bit;

an elevated stop defined in said bore-hole for engaging a portion of a tool bit that is inserted into said bore-hole, wherein said elevated stop comprises:
   a first stop wall that extends from at least one inner side wall of said bore-hole in a direction that is towards the longitudinal axis of said bore-hole; and,
   a second wall the extends from said first stop wall in a direction that is generally parallel to the longitudinal axis of said shaft;
a securing ring receiving slot defined in said outer surface of said shaft, wherein at least a portion of said securing ring receiving slot extends into said bore-hole;
a securing ring, a portion of which is received by said securing ring receiving slot so that at least a portion of said securing ring extends into said bore-hole so that at least a portion of said securing ring contacts a surface of the tool bit that has been inserted into said bore-hole so that said securing ring presses at least a portion of the tool bit towards at least one of said first stop wall and said second stop wall of said elevated stop; and,
whereby when at least a portion of the tool bit is inserted into said bore-hole and at least a portion of said securing ring is placed in said securing ring receiving slot, said elevated stop contacts at least a portion of said tool bit and said securing ring presses at least a portion of the tool bit towards said elevated stop to maintain contact between the tool bit and at least one of said first wall and said second wall of said elevated stop so that rotation of said shaft rotates the tool bit.

11. The hand operated dental instrument of claim 10 wherein said first stop wall extends from said at least one inner side wall of said bore-hole in a direction that is generally perpendicular to the longitudinal axis of said shaft.

12. The hand operated dental instrument of claim 10 wherein said securing ring receiving slot extends into said bore-hole at a point that is generally above said second stop wall of said elevated stop so that said securing ring presses at least a portion of the tool bit against said second stop wall of said elevated stop.

13. The hand operated dental instrument of claim 10 further comprising an access opening disposed in said shaft and is in fluid communication with said securing ring receiving slot for allowing the user to remove said securing ring from within said securing ring receiving slot.

14. The hand operated dental instrument of claim 13, wherein said access opening is in fluid communication with said bore-hole and extends from a point that is generally adjacent to said securing ring receiving slot to said distal end of said shaft.

15. The hand operated dental instrument of claim 10 wherein said securing ring is adjustable so that the pressure that said securing ring applies to at least a portion of the tool bit may be changed.

16. The hand operated dental instrument of claim 10 wherein said shaft extends outwardly from said handle along the longitudinal axis of said handle.

17. A hand operated dental instrument comprising:
a handle;
a shaft carried by said handle, wherein at least a portion of said shaft has an outer surface and an inner surface, wherein said inner surface creates a bore-hole that is adapted to receive a tool bit and extends from a distal end of said shaft towards said handle so that the tool bit may be inserted into at least a portion of said shaft;
an elevated stop defined in said bore-hole for engaging a portion of the tool bit that is inserted into said bore-hole, wherein said elevated stop includes a first stop wall that extends inwardly from said inner surface of said shaft a second stop wall the extends from said first wall so that said second stop wall creates a generally flat surface;
a securing ring receiving slot defined in said outer surface of said shaft, wherein at least a portion of said securing ring receiving slot extends into said bore-hole;
a securing ring, wherein at least a portion of said securing ring is received by said securing ring receiving slot so that at least a portion of said securing ring extends into said bore-hole so that said securing ring contacts a surface of the tool bit that has been inserted into said bore-hole and presses the tool bit towards at least one of said first stop wall and said second stop wall of said elevated stop; and,
whereby when the tool bit is inserted into said bore-hole and at least a portion of said securing ring is placed in said securing ring receiving slot, said elevated stop contacts at least a portion of the tool bit and said securing ring presses at least a portion of the tool bit towards said elevated stop so that rotation of said shaft rotates the tool bit.

18. The hand operated dental instrument of claim 17 wherein said securing ring receiving slot extends into said bore-hole at a point that is generally above said second wall of said elevated stop so that said securing ring presses at least a portion of the tool bit towards said generally flat surface of said second stop wall.

19. The hand operated dental instrument of claim 17 further comprising an access opening that is disposed in said shaft and is in fluid communication with said securing ring receiving slot for allowing the user to remove said securing ring from within said securing ring receiving slot.

20. The hand operated dental instrument of claim 19, wherein said access opening is in fluid communication with said bore-hole and extends from a point that is generally adjacent to said securing ring receiving slot to said distal end of said shaft.

* * * * *